(12) United States Patent
Sachse et al.

(10) Patent No.: US 6,179,853 B1
(45) Date of Patent: Jan. 30, 2001

(54) OSCILLATING BONE HARVESTING DEVICE

(76) Inventors: Hans Sachse; Rainer Sachse, both of Lerchenstrasse 53, 90425 Nuremberg (DE)

(*) Notice: Under 35 U.S.C. 154(b), the term of this patent shall be extended for 0 days.

(21) Appl. No.: 09/249,817

(22) Filed: Feb. 16, 1999

(51) Int. Cl.⁷ ........................................ A61B 17/32
(52) U.S. Cl. ..................... 606/171; 606/169; 600/567
(58) Field of Search .......................... 600/566, 567, 600/568; 606/169, 171, 179

(56) References Cited

U.S. PATENT DOCUMENTS

| | | | |
|---|---|---|---|
| 640,108 | * 12/1899 | Dalzell | 606/179 |
| 5,507,765 | * 4/1996 | Mott | 600/567 |
| 5,922,000 | * 7/1999 | Chodorow | 600/567 |

* cited by examiner

*Primary Examiner*—Michael Buiz
*Assistant Examiner*—Julian W. Woo

(74) *Attorney, Agent, or Firm*—Keil & Weinkauf

(57) ABSTRACT

Bone harvest or bone biopsies so far are made with the use of rotating hollow drills or through axial insertion of a hollow device. Upon retraction of the instrument the problem exists that the bone core often does not detach from its basis and thus cannot be harvested with ease. Additionally, using these methods, often the histology of the bone is disturbed significantly. This problem is solved by this invention by the use of a bone harvesting device which consists of a hollow cylinder, has cutting teeth at one end and has an interior cross-section which is not round. This device can be inserted into the bone using circular oscillation, creating a bone core which has a shape deviating from a strict cylinder shape. Once the desired depth has been achieved, the bone core can be reliably sheared off its basis by rotating the instrument in an angle exceeding the angle of the oscillation.

The bone harvesting device is particularly well suited to obtain bone biopsies and to obtain cancellous bone for transplantation purposes.

However, this device can be used as well for other materials.

7 Claims, 1 Drawing Sheet

OSCILLATING BONE HARVESTING DEVICE

The invention describes a device which is mainly used to obtain bone for diagnostic and therapeutic purposes in medicine. However, a use in other technical areas is possible as well.

BACKGROUND OF THE INVENTION

1. Field of the Invention

Bone harvesting is performed in medicine both for the diagnosis of various diseases as bone biopsies as well as to obtain mainly cancellous bone for auto-transplantation for therapeutic purposes.

2. Description of the Related Art

Besides direct surgical harvest following operative exposure of bone, four different percutaneous methods are currently used to harvest bone:

1) By insertion of a relatively thin, slightly conical needle into the bone which might harvest a small amount of bone upon retraction of the instrument. This method has the disadvantage that only small amounts of bone can be harvested, and that the histological architecture of the bone can be disturbed substantially.

2) By using a cylinder osteotome with a round interior which can be inserted into the bone using rotation or oscillation. Thus a bone core is created which might be retracted with the osteotome as described in G8806721.1. This method has the advantage that excellent bone material can be removed in significant quantities. The disadvantage of this method exists that the bone core tends to stick on its base and thus often can be removed only with substantial difficulties. For this reason the bone harvest has to be made rather deep until soft tissue behind the bone is reached. Another option is the attempt to loosen the bone core by angling and levering the osteotome, which may result in substantial tissue trauma and which nevertheless may not be able to detach the bone core adequately for its removal.

3) By the use of an osteotome which is inserted with a mallet and which consists of a hollow cylinder with an internal ridge. After inserting this osteotome the resulting bone core can be sheared off, due to the existing longitudinal ridge and subsequently be removed easily. The disadvantage of this method is, that a substantial amount of force is necessary to have this osteotome inserted into the bone. Without general anesthesia such a procedure is usually not possible. Additionally the high energy necessary for insertion of these osteotomes, which is usually done with a mallet, may be the cause of substantial soft tissue trauma.

4) Using an osteotome which has one or several teeth reaching into the inner surface of a cylinder as described in International Patent W096/27333 and which may be inserted either using a mallet or by rotation. If this osteotome is inserted with a mallet, the aforementioned disadvantages cannot be avoided. Conversely a substantial amount of bone material is lost, if this osteotome is inserted by rotation. On the other hand, if this osteotome is inserted with too little progression (~less than twice the thickness of the tooth) no adequate retention of the bone core is the result, thus not allowing a removal of the bone core without substantial manipulation and above mentioned disadvantages.

The purpose of this invention is to develop a bone harvesting device thus that bone can be obtained in substantial quantities easily, reliably and without substantial destruction of the bone structure.

BRIEF SUMMARY OF THE INVENTION

To achieve this task this bone harvesting device is based on insertion of a cylindrical device by oscillation and which has an interior lumen, which is not round. A set of cutting teeth at its one end allows its insertion into bone with relatively little force and tissue trauma. Once the desired depth has been reached, the device is rotated by an angle exceeding the angle of the oscillation. By this rotation, the bone core is reliably sheared off its base and can subsequently be removed together with the instrument. This circular oscillating motion can be created both manually as well as using a mechanical or electrical motor with appropriate gears. The latter option is preferred due to the higher speed and greater precision. Subsequently, the bone core can be easily ejected from the osteotome with the help of a pusher rod.

BRIEF DESCRIPTION OF THE DRAWINGS

A preferred example is depicted in FIGS. 1–3.

DETAILED DESCRIPTION OF THE DRAWINGS

Figure 1:
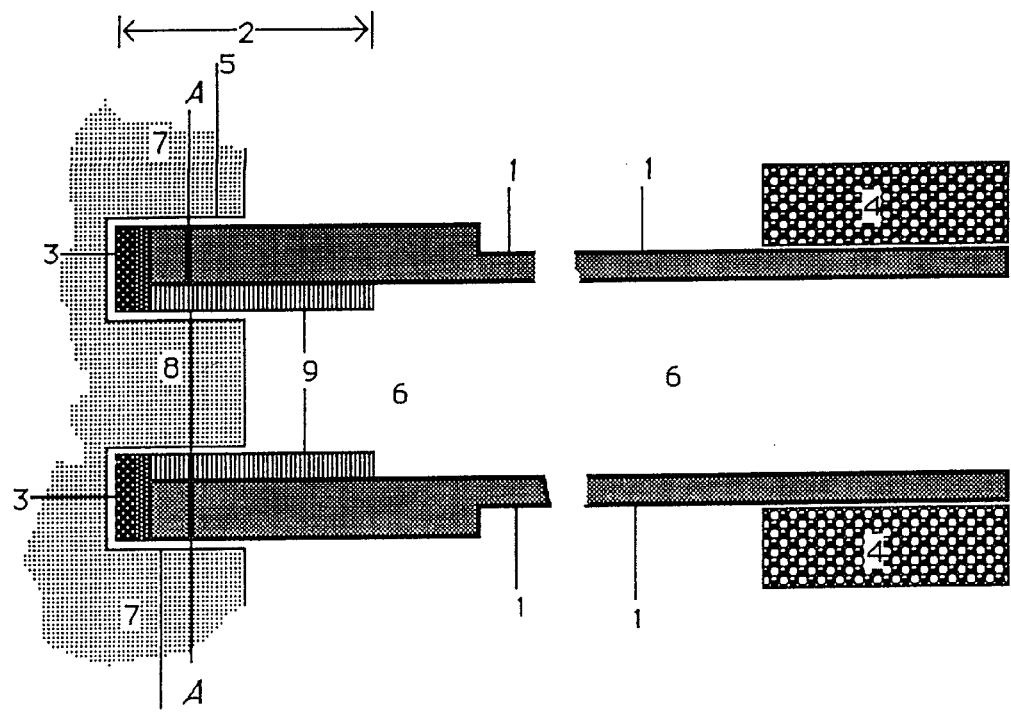
FIG. 1 shows a longitudinal section through the bone harvesting device.

FIG. 1: the bone harvesting device consists of a shaft (1) of a hollow cylinder and the working part (2) which has cutting teeth (3) at its end. Two ridges (9) reach into the interior lumen, and down to the cutting teeth and usually have one or several cutting teeth themselves. Once the cutting teeth are propelled with an oscillating motion they cut themselves into the bone (7), creating a bone core (8), which has a shape correlating to the oscillating motion and the ridge (8) in the depicted shape. For propulsion, a manual handle (4) can be used.

Figure 2:
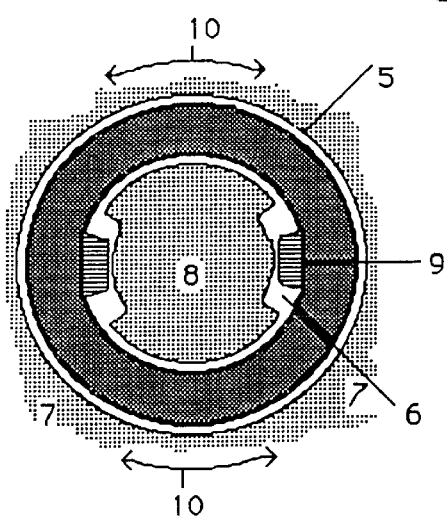
FIG. 2 shows a transverse section through the working part of the bone harvesting device according to line a—a in FIG. 1.

FIG. 2: This figure shows a transverse section of FIG. 1 depicting line a—a. Two ridges (9) reach into the interior lumen (6). The arrows (10) show the direction of the oscillating motion. The bone core (8) has been formed by the oscillating motion creating a somewhat larger hole in the bone (5).

Figure 3:
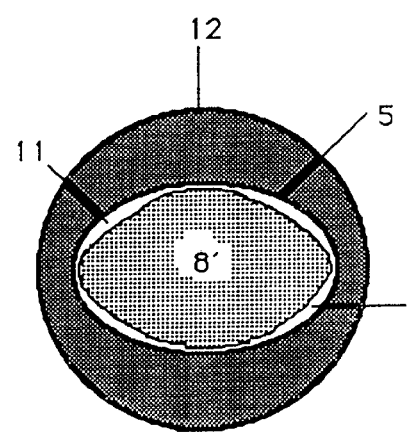
FIG. 3 shows a transsection through an alternative bone harvesting device using an oval interior lumen.

FIG. 3: The example depicted in FIG. 3 shows a transsection through the working part of a different alternative of the bone harvesting device (12) with the bone core it creates. The interior surface has an oval cross-section which creates an oval bone core (8) through its oscillating motion. Again, the bone harvesting device is driven into the bone by an oscillating motion and the bone core is sheared off once the desired depth has been reached. Once the bone core has been sheared off its base it can be easily retracted with the instrument.

What is claimed is:

1. A bone harvesting device consisting of
   a) a hollow cylinder having a first and a second axial end and a shaft extending from the first to the second end, which cylinder comprises an interior lumen extending from the first to the second end, and the first end of which cylinder has cutting teeth extending longitudinally from said end, and
   b) means adapted to propel the cylinder around its longitudinal axis in a circularly oscillating motion, which means is attached to the second end of the cylinder, wherein the lumen of the cylinder a) has a cross-section which is not circular and which is adapted to provide, upon insertion of the cylinder into a bone by circular oscillation of the cylinder, a non-cylindrical bone core.

2. The device defined in claim 1, wherein the means b) is a handle adapted to apply the oscillating motion of the cylinder manually.

3. The device defined in claim 1, wherein the means b) is a mechanical, electrical or electronic propulsion system.

4. The device defined in claim 1, wherein the means b) is further adapted to create an oscillating motion of the cylinder along the longitudinal axis for insertion of the cylinder into a bone.

5. The device defined in claim 1, wherein the hollow cylinder includes one or more ridges extending into the interior lumen and longitudinally extending from the first end of the cylinder, which ridges render the cross section of said lumen non-circular.

6. The device defined in claim 1, wherein the cross-section of the lumen is oval.

7. The device defined in claim 6, wherein the ridges comprise cutting teeth extending longitudinally from the first end of the cylinder.

* * * * *